United States Patent [19]

Todd et al.

[11] 4,172,120

[45] Oct. 23, 1979

[54] CHOLESTYRAMINE COMPOSITIONS AND METHOD FOR TREATING BILIARY GASTRITIS

[75] Inventors: Richard S. Todd, Cottingham; Gordon R. Fryers, Oxted, both of England

[73] Assignee: Reckitt & Colman Products Limited, London, England

[21] Appl. No.: 884,855

[22] Filed: Mar. 9, 1978

[30] Foreign Application Priority Data

Mar. 10, 1977 [GB] United Kingdom ............... 10133/77

[51] Int. Cl.² .................. A61K 9/46; A61K 31/74; A61K 47/00
[52] U.S. Cl. ........................... 424/44; 424/34; 424/35; 424/43; 424/78; 424/79
[58] Field of Search .................... 424/34, 35, 43, 44, 424/78, 79

[56] References Cited

U.S. PATENT DOCUMENTS

| | | | |
|---|---|---|---|
| 3,369,944 | 2/1968 | Sandmark | 424/4 |
| 3,499,960 | 2/1970 | Macek | 424/33 |
| 3,769,399 | 10/1973 | Hagerman | 424/79 |
| 3,974,272 | 8/1976 | Polli | 424/78 |
| 4,079,125 | 3/1978 | Sipos | 424/35 |

FOREIGN PATENT DOCUMENTS 980237 1/1965 United Kingdom .

OTHER PUBLICATIONS

Martindale, Extra Pharm., Pharm. Press, London, 26th ed., pp. 127 and 2050.
Whistler, Industrial Gums, Acd. Press, N. Y., 1959, pp. 68–69.

*Primary Examiner*—Anna P. Fagelson
*Attorney, Agent, or Firm*—Bacon & Thomas

[57] ABSTRACT

A solid pharmaceutical composition comprising anhydrous cholestyramine, 0.6 to 1.7 parts by weight of low viscosity grade alginic acid/sodium alginate per weight of cholestyramine, the low viscosity grade alginic acid/sodium alginate having 0 to 75% of the acid groups neutralized, 0.1 to 0.3 parts by weight of citric acid per weight of sodium alginate, and sufficient sodium carbonate or bicarbonate mixtures thereof to neutralize the acid groups of the alginic and citric acids. The compositions may be used in the treatment of conditions associated with duodeno-gastric reflux of bile into the stomach.

8 Claims, 1 Drawing Figure

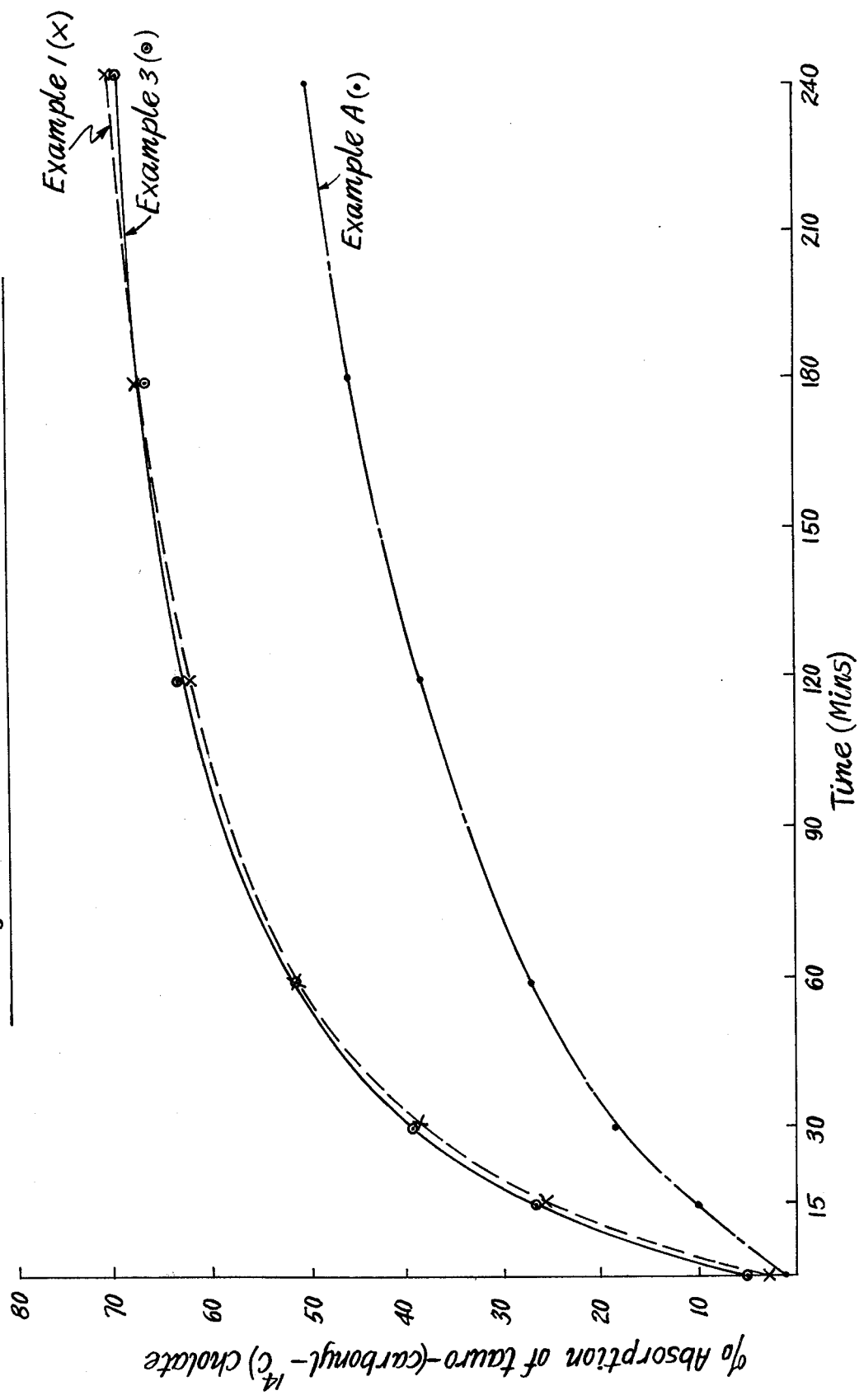

CHOLESTYRAMINE COMPOSITIONS AND METHOD FOR TREATING BILIARY GASTRITIS

This invention relates to pharmaceutical compositions and in particular to compositions for use in the treatment of those conditions in man associated with the duodeno-gastric reflux of bile into the stomach. Such conditions include biliary gastritis and bile-induced gastric ulceration.

Cholestyramine, which is a polystyrene-divinylbenzene copolymer anion exchange resin, has been used to bind bile acids in the intestine, in those patients in whom excessive levels of bile leads to conditions such as hypercholesterolaemia and pruritis. The cholestyramine exchanges chloride ions for the bile which it binds into an insoluble complex that is excreted in the faeces, so preventing the normal re-absorption of bile salts. High dosing can lead to constipation, diarrhoea and steatorrhoea.

Cholestyramine has been used in the treatment of gastric ulceration associated with duodeno-gastric reflux of bile, with little success. It has been suggested that this lack of success is due to the fact that the cholestyramine is retained in the stomach for too short a period of time.

We have now developed a preparation including cholestyramine which is retained in the stomach for a greater period of time and is therefore more effective in binding refluxed bile.

According to this invention there is provided a solid pharmaceutical composition comprising anhydrous cholestyramine, 0.6 to 1.7 parts by weight of low viscosity grade alginic acid/sodium alginate per weight of cholestyramine, the low viscosity grade alginic acid/sodium alginate having 0 to 75% of the acid groups neutralised and for which the viscosity of a neutralised 1% aqueous solution, when determined on a Brookfield viscometer model LVF using spindle No. 1 at 60 r.p.m. at 25° C. is within the range of from 4 to 30 centipoises, 0.1 to 0.3 parts by weight of citric acid per weight of sodium alginate, and sufficient sodium carbonate or bicarbonate or mixtures thereof to neutralise the acid groups of the alginic and citric acids.

In a preferred composition the low viscosity grade alginic acid/sodium alginate is present in an amount of from 0.9 to 1.4 parts by weight per weight of cholestyramine.

Alginic acid and its salts such as sodium alginate, which are extracted from brown algae, are composed of 1,4′-linked residues of $\beta$-D-mannuronic acid and $\alpha$-L-guluronic acid in varying proportions according to the source of the brown algae and the method of extraction. As a polycarboxy acid alginic acid can form a series of partial salts. By alginic acid/sodium alginate in which 0 to 75% of the acid groups are neutralised is contemplated not only mixtures of alginic acid with sodium alginate blended in the appropriate ratios to give the specified percentages of neutralised acid groups, but also partial salts with the specified percentages of neutralised acid groups. Thus for example an alginic acid/sodium alginate in which 50% of the acid groups are neutralised may comprise a 50/50 mixture of alginic acid with sodium alginate, or a partial salt with 50% of the acid groups neutralised. One of the most useful properties of the water-soluble alginates is their ability to form viscous solutions at low concentrations. Because of the varied composition of the alginates different alginates at the same concentration give solutions of differing viscosity. By the term "low viscosity grade alginic acid/sodium alginate" as used herein is meant those grades of alginic acid/sodium alginate for which the viscosity of a 1% aqueous solution, when determined on a Brookfield viscometer model LVF using spindle No. 1 at 60 r.p.m. at 25° C., falls within the range of from 4 to 30 centipoises. Where alginic acid or a partially neutralised alginic acid is used, these are first converted to sodium alginate before the viscosity measurement is made (by adding sodium hydroxide).

Examples of suitable commercial grades of alginic acid include:

alginic acid HFD2 (Alginate Industries, U.K.) which typically has a viscosity of 15–25 centipoises, Protacid F 120 (Protan & Fagertun, Norway) which typically has a viscosity of 15–25 cps, Kelacid (Kelco, U.S.A.) which typically has a viscosity of 10–20 cps, and Algocean (Sobalg, France) which typically has a viscosity of 15–25 cps.

Examples of suitable commercial grades of sodium alginate include:

Manucol LD (Alginate Industries) which typically has a viscosity of 10 cps,

Manucol LF (Alginate Industries) which typically has a viscosity of 20 cps,

Protanal LF 5/60 or LF 5/40 (Protan & Fagertun) both of which typically have a viscosity of 10 cps, and Protanal LF 5/120 M which typically has a viscosity of 20 cps.

An example of a partially neutralised alginic acid is one coded PE III (Protan & Fagertun) which is approximately 50% neutralised and has typically a viscosity of 15 cps.

In all the above examples the viscosity of a 1% solution (as determined by the specified method) falls below 30 cps. It is possible to use in the compositions of the invention grades of sodium alginate such as Manucol LHF and Protanal LF 10/120, where viscosity of a 1% solution is slightly greater than 30 cps (both typically 40 cps), if they are blended with alginic acid or other grades of sodium alginate (having a viscosity of a 1% solution less than 30 cps) when the viscosity of the blend is less than 30 cps. Thus for example a 40/60 blend of Manucol LF with Manucol LHF has a viscosity of 24 cps.

Cholestyramine resin is a strongly basic anion-exchange resin in the chloride form, consisting of a styrene-divinyl-benzene copolymer with quaternary ammonium functional groups. USP quality material is in the form of a fine powder containing 5–12% moisture.

Examples of suitable commercial grades of cholestyramine include:

Cuemid (Merck, Sharp & Dohme Ltd, approximately 85% anhydrous cholestyramine resin).

Amberlite XE-268P (Rohm & Haas, approximately 90% anhydrous cholestyramine resin).

Dowex 1×2- Cl (Dow Chemical Co., U.S.A., wet beads containing about 75% moisture).

Those grades in the form of wet beads require to be dried and milled before incorporation into the compositions of the invention.

The solid pharmaceutical compositions of the present invention may be presented in the form of dry powders, granules, and tablets. They may include excipients such as for example calcium phosphate, microcrystalline cellulose, lactose, sucrose, dextrose or mannitol, particularly preferred is a mixture of sucrose and mannitol. Preparations in the form of granules and tablets will additionally include binding agents such as polyvinylpyrrolidone or acacia. Tablets may also include lubricating agents such as magnesium stearate and/or glidants such as talc. The compositions may also include one or more flavouring or colouring agents.

For the ease of dosing the compositions in the form of granules or powders are conveniently packaged in sachets. A convenient unit dose of the composition in a sachet in the form of granules or powder will comprise 0.7 to 1.0 g of anhydrous cholestyramine, 0.6 to 1.7 parts by weight per weight of cholestyramine of low viscosity grade alginic acid/sodium alginate (as hereinbefore defined) in which 0 to 75% of the acid groups are neutralised, 0.1 to 0.3 parts by weight of citric acid per weight of sodium alginate, and sufficient sodium carbonate or bicarbonate or mixtures thereof to neutralise the acid groups of the alginic and citric acids.

Tablets will comprise 0.35 to 0.50 g of anhydrous cholestyramine, 0.6 to 1.7 parts by weight per weight of cholestyramine of low viscosity grade alginic acid/sodium alginate (as hereinbefore defined) in which 0 to 75% of the acid groups are neutralised, 0.1 to 0.3 parts by weight of citric acid per weight of sodium alginate, and sufficient sodium carbonate or bicarbonate or mixtures thereof to neutralise the acid groups of the alginic and citric acids.

The compositions in the form of tablets or granules are well chewed and, on chewing the sodium carbonate and/or bicarbonate reacts with the acid components of the composition in the presence of saliva in the buccal cavity to produce carbon dioxide and a viscous solution of sodium alginate which serves to coat the particles of cholestyramine and hence to ameliorate the unpleasant taste and mouth-feel of cholestyramine. The resultant sticky mass on being swallowed reacts further with gastric acid to form a carbonated raft of alginic acid which floats on the contents of the stomach. The raft is of such a consistency that whilst it holds the cholestyramine the cholestyramine is sufficiently loosely held as to be able to absorb bile acid present in the stomach.

The compositions in the form of powders are added to a small amount of water and the resultant mixture swallowed.

The invention is illustrated by the following non-limiting Examples:

EXAMPLE 1

A preparation in the form of granules was prepared from the following formulation:

| | |
|---|---|
| alginic acid (HFD 2) | 1000 g |
| sodium bicarbonate | 370 g |
| cholestyramine (Cuemid) | 1000 g |
| sucrose | 2000 g |
| mannitol | 1258 g |
| polyvinylpyrrolidone | 140 g |
| peppermint oil | 6 g |

All the ingredients except the polyvinylpyrrolidone and peppermint oil were sieved and blended, and then mixed with a solution in isopropanol of the polyvinylpyrrolidone and peppermint oil in a planetary mixer. The resultant cohesive mass was granulated through a 1.4 mm (B.S.S.) sieve, and the granules dried at 50° C. to remove isopropanol. Undersize material was removed on a 500 μm (B.S.S.) sieve, and the product packaged into unit dose sachets, each containing approximately 0.85 g of anhydrous cholestyramine resin.

EXAMPLE 2

A preparation in the form of granules, was prepared by the method of Example 1, from the following formulation:

| | |
|---|---|
| partially neutralised alginic acid (PE III) | 1080 g |
| sodium bicarbonate | 300 g |
| cholestyramine (Cuemid) | 1000 g |
| citric acid | 100 g |
| sucrose | 2000 g |
| mannitol | 1258 g |
| polyvinylpyrrolidone | 140 g |
| peppermint oil | 6 g |

EXAMPLE 3

A preparation in the form of granules, was prepared by the method of Example 1, from the following formulation:

| | |
|---|---|
| sodium alginate (Protanal LF 5/120M) | 500 g |
| alginic acid (Protacid F 120) | 500 g |
| sodium bicarbonate | 305 g |
| cholestyramine (Cuemid) | 1000 g |
| citric acid | 100 g |
| sucrose | 2000 g |
| mannitol | 1258 g |
| polyvinylpyrrolidone | 140 g |
| peppermint oil | 6 g |

EXAMPLE 4

A preparation in the form of tablets was prepared from the following formulation:

| | |
|---|---|
| alginic acid (HFD 2) | 800 g |
| sodium bicarbonate | 296 g |
| cholestyramine (Cuemid) | 1000 g |
| sucrose | 2000 g |
| mannitol | 1248 g |
| polyvinylpyrrolidone | 90 g |
| peppermint oil | 6 g |
| magnesium stearate | 84 g |

All the ingredients except the magnesium stearate were processed by the method of Example 1 to produce granules. The dried granules were comminuted through a 1.4 mm (B.S.S.) sieve, the magnesium stearate was blended into the mixture, and the resultant product compressed into tablets, each tablet containing approximately 0.42 of anhydrous cholestyramine resin.

EXAMPLES 5 to 11

The formulation of the granules of Example 3 was varied by employing differing quantities of sodium alginate (see below), alginic acid (HFD 2), sodium bicarbonate, cholestyramine (Cuemid) and citric acid, whilst using the same quantities of sucrose, mannitol, polyvinylpyrrolidone and peppermint oil.

| | 5 | 6 | 7 | 8 | 9 | 10 | 11 | |
|---|---|---|---|---|---|---|---|---|
| sodium alginate | 750$^a$ | 750$^a$ | 400$^b$ | 600$^b$ | 250$^c$ | — | — | g |

-continued

|  | 5 | 6 | 7 | 8 | 9 | 10 | 11 | |
|---|---|---|---|---|---|---|---|---|
| alginic acid | 250 | 250 | 400 | 600 | 750 | 800 | 1200 | g |
| sodium bicarbonate | 213 | 333 | 268 | 342 | 308 | 296 | 444 | g |
| cholestyramine | 1000 | 1000 | 1000 | 1000 | 1000 | 1000 | 1000 | g |
| citric acid | 100 | 200 | 100 | 100 | 25 | — | — | g |

$^a$ = Protanal LF5/60;
$^b$ = Manucol LF;
$^c$ = Protanal LF10/120.

EXAMPLE 12

The formulation of the granules of Example 1 was varied by replacing the sodium bicarbonate by 234 g of sodium carbonate.

EXAMPLE 13

The formulation of the granules of Example 3 was varied by replacing the grade of sodium alginate used therein by 500 g of a 50/50 blend of Manucol LF (viscosity approximately 20 cps) and Manucol LHF (viscosity approximately 40 cps) the blend having a viscosity approximately 30 cps.

EXAMPLE 14

The formulation of the granules of Example 2 was varied by replacing the grade of cholestyramine used therein by 1000 g of Amberlite XE-268 P.

EXAMPLE 15

The formulation of the granules of Example 3 was varied by replacing the grade of cholestyramine used therein by 1000 g of Amberlite XE-268 P.

The following comparative Examples A to D are of preparations in the form of granules which do not fall within the scope of the present invention.

EXAMPLE A

The formulation of the granules of Example 3 was varied by replacing the grade of sodium alginate used therein by 500 g of Manucol LH (viscosity approximately 50 cps) and the grade of alginic acid by 500 g of the alginic acid HFD 2.

EXAMPLE B

The formulation of the granules of Example 1 was varied by replacing the grade of alginic acid used therein by 1000 g of an alginic acid grade, which grade as a 1% solution had a viscosity of approximately 3 cps.

EXAMPLE C

The formulation of the granules of Example 1 was varied by employing 200 g of alginic acid and 74 g of sodium bicarbonate.

EXAMPLE D

The formulation of the granules of Example 3 was varied by employing differing quantities:

| sodium alginate (Protanal LF 5/120M) | 1000 g |
|---|---|
| alginic acid (Protacid F 120) | 1000 g |
| sodium bicarbonate | 490 g |

As has been previously indicated the preparations after swallowing by the patient react with the gastric acid to form a carbonated raft which then floats on the stomach contents. It will be appreciated that if the resultant alginic acid gel is inadequately carbonated a raft will not be formed and consequently the alginic acid and cholestyramine will remain in the stomach for insufficient time for adequate binding of bile to occur. Thus in order to prolong the residence time of the cholestyramine in the stomach a raft must be formed which floats on the surface of the stomach contents remaining integral for a period of several hours and having sufficient strength to hold the cholestyramine. Since the cholestyramine must be held in the gel matrix of the raft yet must also be available to bind bile acids, the permability of the raft is critical.

An in vitro test employing a radio-tracer technique has been devised in order to monitor these criteria, and, with respect to Example 1, this was carried out in the following manner.

An amount of the preparation containing about 0.42 g anhydrous cholestyramine (one half of a unit dose) was mixed with 11 ml of water and added to 100 ml of 0.1 N hydrochloric acid; 10 ml of a 2.5% solution of radio-labelled sodium taurocholate of activity 0.03 $\mu$Ci/ml as tauro-(carbonyl-14C) cholate was injected into the acid below the raft. The mixture was shaken gently at 37° for 4 hrs, samples being taken at suitable time intervals and processed to determine their level of radioactivity, the resultant taurocholate absorption data being presented graphically. In addition, the rafts were assessed initially, and at the completion of the assay procedure, with reference to raft size, strength, and permeability, and to cholestyramine loss from the raft.

The raft obtained in Example 1 was deemed in the subjective assessment of raft rigidity to be of adequate strength and permeability and covered the whole surface of the acid. It remained integral throughout the in vitro test with no significant deposition of cholestyramine from the raft.

The rigidity of the rafts formed by the preparations of the other Examples and the Comparative Examples are described below in relation to the rigidity of the raft of Example 1.

| Example No. | Comments |
|---|---|
| 2 | Similar to Example 1, although slightly less carbonated. |
| 3 | Similar to Example 1, but a slightly stronger and less carbonated raft. |
| 4 | Similar to Example 1, but a slightly weaker and less carbonated raft. |
| 5 | Similar to Example 1, but a somewhat weaker and less carbonated raft. |
| 6 | Similar to Example 1, but a somewhat weaker raft. |
| 7 | Similar to Example 1, but a slightly weaker and less carbonated raft. |
| 8 | Similar to Example 1, but a slightly stronger raft. |
| 9 | Similar to Example 1, but a slightly stronger and less carbonated raft. |
| 10 | Similar to Example 1, but a slightly weaker and less carbonated raft. |
| 11 | Similar to Example 1, but a slightly |

| Example No. | Comments |
| --- | --- |
| | stronger and more carbonated raft. |
| 12 | Similar to Example 1, but a somewhat stronger and less carbonated raft. |
| 13 | Similar to Example 1, but a somewhat stronger and slightly less carbonated raft. |
| 14 | Similar to Example 1, although slightly less carbonated. |
| 15 | Similar to Example 1, but a slightly stronger and lss carbonated raft. |
| A | The raft was discontinuos, more compact and rigid than Example 1, and was of inadequate permeability. |
| B | The raft was weak and agitation caused disintegration, with extensive deposition of cholestyramine. |
| C | The raft was weak and agitation caused disintegration, with extensive deposition. |
| D | The raft was discontinuous, more compact and rigid than Example 1, and was of inadequate permeability. |

FIG. 1 presents the graphs obtained for the binding of taucholate with the preparations of Examples 1 and 3, and also comparative Example A. With Examples 1 and 3 it can be seen that the absorption over 4 hours builds up to about 65% whilst with the comparative Example A, which contains exactly the same amount of cholestyramine, over 4 hours it only reaches a level of about 45% thus showing the improved performance of the two Examples of the invention over the comparative Example.

What we claim is:

1. A solid pharmaceutical composition comprising anhydrous cholestyramine, 0.6 to 1.7 parts by weight of low viscosity grade alginate material selected from the group consisting of alginic acid, sodium alginate, partial salts of alginic acid and mixtures thereof per weight of cholestyramine, the low viscosity grade alginate material having 0 to 75% of the acid groups neutralised and for which the viscosity of a neutralised 1% aqueous solution, when determined on a Brookfield viscometer model LVF using spindle No. 1 a 60 r.p.m. at 25° C. is within the range of from 4 to 30 centipoises, 0.1 to 0.3 parts by weight of citric acid per weight of sodium alginate, and sufficient sodium carbonate or bicarbonate or mixtures thereof to neutralise the acid groups of the alginic and citric acids.

2. A solid pharmaceutical composition as claimed in claim 1 wherein the low viscosity grade alginate material is present in an amount of from 0.9 to 1.4 parts by weight per weight of cholestyramine.

3. A solid pharmaceutical composition as claimed in claim 1 in unit dosage form in a sachet in the form of granules or powders comprising 0.7 to 1.0 g of anhydrous cholestyramine, 0.6 to 1.0 g of anhydrous cholestyramine, 0.6 to 1.7 parts by weight of low viscosity grade alginate material per weight of cholestyramine, 0.1 to 0.3 parts by weight of citric acid per weight of sodium alginate, and sufficient sodium carbonate or bicarbonate or mixtures thereof to neutralise the acid groups of the alginic and citric acids.

4. A solid pharmaceutical composition as claimed in claim 1 in the form of a tablet comprising 0.35 to 0.50 g of anhydrous cholestyramine, 0.6 to 1.7 parts by weight of alginate material per weight of cholestyramine, 0.1 to 0.3 parts by weight of citric acid per weight of sodium alginate, and sufficient sodium carbonate or bicarbonate or mixtures thereof to neutralise the acid groups of the alginic and citric acids.

5. A solid pharmaceutical composition as claimed in claim 1 wherein the low viscosity grade alginate material is a mixture of approximately equal amounts of alginic acid and sodium alginate.

6. A pharmaceutical composition as claimed in claim 1 wherein the viscosity grade alginate material is a partially neutralised alginic acid which is approximately 50% neutralised.

7. A solid pharmaceutical composition as claimed in claim 1 wherein the low viscosity grade alginate material is alginic acid.

8. A method of treating biliary gastritis comprising orally administering to a human suffering from biliary gastritis an effective amount therefor of the solid pharmaceutical composition as defined by claim 1.

UNITED STATES PATENT OFFICE
CERTIFICATE OF CORRECTION

Patent No. 4,172,120             Dated   October 23, 1979

Inventor(s) Richard S. TODD ET AL

It is certified that error appears in the above-identified patent and that said Letters Patent are hereby corrected as shown below:

IN THE CLAIMS:

Claim 3, column 8, delete "0.6 to 1.0 g of anhydrous cholestyramine," from lines 12 and 13.

Signed and Sealed this

Nineteenth Day of February 1980

[SEAL]

Attest:

SIDNEY A. DIAMOND

Attesting Officer       Commissioner of Patents and Trademarks